US008005528B2

(12) United States Patent
Long (10) Patent No.: US 8,005,528 B2
(45) Date of Patent: Aug. 23, 2011

(54) APPARATUS FOR ELUCIDATING REACTION DYNAMICS OF PHOTOREACTIVE COMPOUNDS FROM OPTICAL SIGNALS AFFECTED BY AN EXTERNAL MAGNETIC FIELD

(75) Inventor: William F. Long, Quebec (CA)

(73) Assignee: Institut National d'Optique, Sainte-Foy, Quebec (CA)

( * ) Notice: Subject to any disclaimer, the term of this patent is extended or adjusted under 35 U.S.C. 154(b) by 0 days.

(21) Appl. No.: 12/398,593

(22) Filed: Mar. 5, 2009

(65) Prior Publication Data

US 2009/0198114 A1    Aug. 6, 2009

Related U.S. Application Data

(63) Continuation of application No. 10/671,704, filed on Sep. 26, 2003, now Pat. No. 7,519,411.

(51) Int. Cl.
*A61B 5/05*    (2006.01)

(52) U.S. Cl. ........ 600/407; 600/473; 600/475; 600/476; 600/477; 600/478

(58) Field of Classification Search .................. 600/407, 600/473, 475, 476–478
See application file for complete search history.

(56) References Cited

U.S. PATENT DOCUMENTS

| 5,853,370 A | 12/1998 | Chance et al. | |
|---|---|---|---|
| 5,921,244 A * | 7/1999 | Chen et al. | 128/897 |
| 6,128,525 A * | 10/2000 | Zeng et al. | 600/476 |
| 6,514,277 B1 | 2/2003 | Lilge et al. | |
| 6,544,193 B2 | 4/2003 | Abreu | |
| 6,679,827 B2 | 1/2004 | Sandstrom | |
| 2003/0083537 A1* | 5/2003 | Ardizzone | 600/9 |

OTHER PUBLICATIONS

Hoff et al. "Magnetic Field Effect on Photosynthetic Reactions." *Biological Effects of Steady Magnetic Fields*. Dept. of Biophysics, Huygens Laboratory of the State University, The Netherlands; 1986, pp. 74-84.

Henderson et al., *Mechanistic Principles of Photodynamic Therapy*. Roswell Park cancer Institute, Buffalo New York; pp. 36-1 to 36-14.

Herman et al. "Lifetime-Based Imaging." *Biomedical Photonics Handbook*, pp. 9-1 to 9-18.

* cited by examiner

*Primary Examiner* — Brian Casler
*Assistant Examiner* — James Kish
(74) *Attorney, Agent, or Firm* — Merchant & Gould P.C.

(57) ABSTRACT

A device elucidates reaction dynamics of photoreactive compounds present in a region of interest (ROI) of a tissue, the ROI being submitted to a controllably-varying and spatially homogenous magnetic field. The device includes at least one electrical coil or magnet for externally applying a magnetic field to the ROI. The device further includes light sources for probing the ROI with a probe optical beam and for illuminating the ROI with an optical beam having a wavelength and power level suitable for activating the photoreactive compounds. Collectors are also provided to collect the light emitted from various photoluminescence mechanisms that occur in the optically-activated ROI when the probe beam is incident on it and then to detect the collected light over predetermined wavelength bands. Finally, a computer is used to analyze the detected light for assessing the effects of the external magnetic field applied to the ROI.

10 Claims, 7 Drawing Sheets

APPARATUS FOR ELUCIDATING REACTION DYNAMICS OF PHOTOREACTIVE COMPOUNDS FROM OPTICAL SIGNALS AFFECTED BY AN EXTERNAL MAGNETIC FIELD

This application is a continuation of Ser. No. 10/671,704, filed Sep. 26, 2003, and which application is incorporated herein by reference. To the extent appropriate, a claim of priority is made to the above disclosed application.

FIELD OF THE INVENTION

The present invention is directed to an apparatus and method for elucidating reaction dynamics of photoreactive compounds from optical signals affected by an external magnetic field.

BACKGROUND

Figure 1:
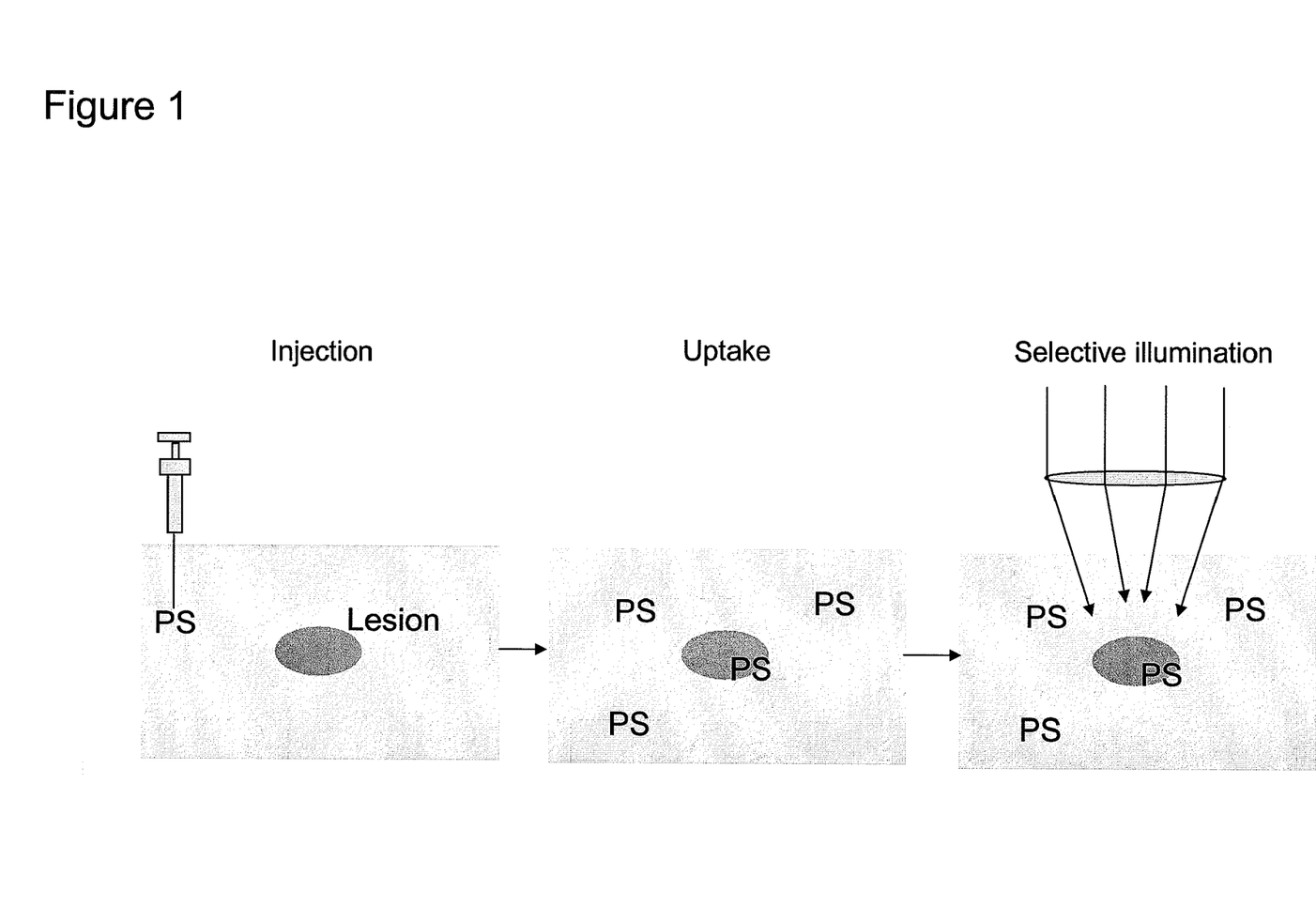
FIG. 1 (Prior art) is a schematic representation of the basic mechanism of PDT.
Figure 2:
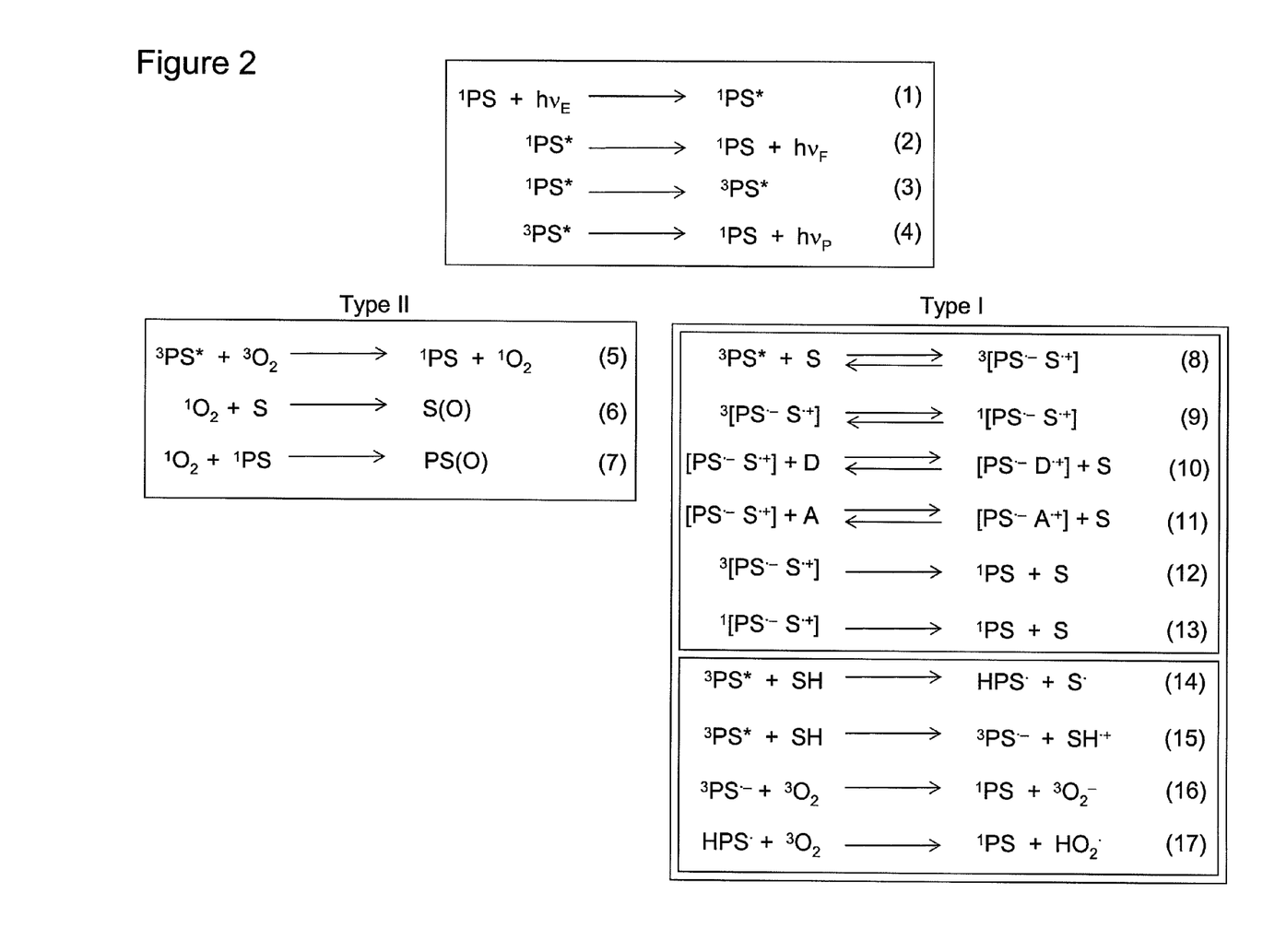
FIG. 2 (Prior art) shows the Type I and Type II reaction pathways for PDT.

Known in the art is a relatively recent method of treatment known as photodynamic therapy. During photodynamic therapy (PDT), a photosensitizer is introduced into an organism and is activated by light to induce cytotoxicity as shown in FIG. 1. The activated photosensitizer reacts with oxygen species producing singlet oxygen, which then react with tissue. A simplistic scheme for this reaction may be written as, $$^1PS + h\nu \rightarrow {}^3PS^* + {}^3O_2 \rightarrow {}^1O_2^* + S \rightarrow S(O)$$

where $^1PS$ is the ground state photosensitizer, hv is a photon of light, $^3PS^*$ is the photosensitizer in the excited triplet state, $^1O_2^*$ is singlet oxygen and S is the biological substrate. More generally, the reaction dynamics follow Type I or Type II pathways to varying extents, as shown in FIG. 2.

The medicinal effect of a PDT photosensitizer (PS) occurs after the substance absorbs light and enters an excited state (reaction step 1). A portion of this energy is released immediately in the form of fluorescent emissions (reaction step 2), while other phosphorescent emissions (reaction step 4) occur after the excited PS converts from a singlet to a triplet state via inter-system crossing (reaction step 3). Typically, the PS triplet state may interact with ground state oxygen molecules, $O_2$ ($^3\Sigma_u$), present in tissue to yield cytotoxic singlet state oxygen, ($^1\Delta_g$), via the Type II pathway (reaction steps 5 and 6). This energetic form of oxygen then rapidly reacts with proteins, lipids and DNA (denoted by S in FIG. 2) yielding tissue damage. Additionally, singlet oxygen may react with the photosensitizer itself in a process known as photobleaching (reaction step 7). The PS triplet state may also react via the Type I pathway with other species that initially form radicals and radical ion pairs (reactions steps 8 through 17). These radicals may react with oxygen leading to the production of other cytotoxic compounds such as superoxides (reaction step 16) and the hydrogen dioxide radical anion (reaction step 17). Since oxygen rapidly quenches the excited triplet state of the PS, the Type II mechanism dominates the overall reaction. The reader should appreciate that the reaction schemes covered by the teachings of FIG. 2 are only exemplary and by no means represent the totality of all pathways and do not represent a sequence of mechanistic steps.

After introducing a photosensitive agent into the body, it may remain in its free state or bind to proteins and DNA. These binding processes have an effect on the excited singlet and triplet state lifetimes of the PS and generally complicate optical schemes for in vivo monitoring during photodynamic therapy. During treatment, the physico- and bio-chemical behaviour of photosensitive agents are also quite variable. The effects of photobleaching, tissue oxygenation along with changes in the local chemical environment and protein-binding characteristics of a PS limit the efficacy of photodynamic treatment. Additionally, some PS compounds prefer to collect in the vascular system, while others preferentially concentrate in the lysosomes and near the mitochondria of certain cancerous cells. Since PS bio-uptake and chemistry affects treatment efficacy, drug formulation, and light dosing must be optimized. Unfortunately, the effectiveness of a photodynamic therapy session is usually not evident until after treatment. Furthermore, researchers involved in developing new PDT compounds often have no real time or direct way of knowing how well a drug performs in vivo. Presently, one determines the effectiveness of the drug by evaluating changes in tumour size, the extent of cell apoptosis and tissue necrosis and immune response with analytical bioassays.

In order to better understand the direct chemical reaction dynamics of a PDT compound, several researchers have started to monitor luminescent emissions from tissue during treatment. By measuring the oxygen concentration electrochemically (with the aid of a minimally invasive oxygen electrode), researchers have found a correlation between the change in phosphorescence lifetime or total luminescence intensity with tissue oxygen concentration. This method however is not ideal and produces biased results. Additionally, only the overall oxygen consumption rate in tissue is measured. Other researchers have tried to measure the luminescent emissions of singlet oxygen at 1269 nm, which may directly measure the reaction rate via the Type II pathway. However this measurement is extremely difficult to perform quantitatively in vivo due to the masking effect of other luminophores and absorbers present in this wavelength region.

Other approaches for estimating the extent of a photodynamic reaction via the Type II pathway appear possible and are, in part, the subject of the present invention.

In literature pertaining to the effect of extremely low frequency (~50 Hz) electromagnetic fields on the efficacy of a photodynamic treatment, it is known that field strengths of 6 millitesla (mT) may enhance cell death by 20 to 40%. In literature pertaining to the effect of magnetic fields on chemical kinetics, it is known that radical ion pairs, neutral radicals and the potential energy surfaces of triplet-triplet annihilation reactions may be affected by an external magnetic field. A review of pertinent chemical literature has revealed that triplet-triplet annihilation reactions between planar metallophthalocyanine moieties are mildly affected by strong magnetic fields (~7 T). The literature also suggests that the production of free uncharged radical pairs in solution is mildly affected by weak to medium strength magnetic fields (<0.5 T). In general, these reactions include those of reaction steps 14 and 17 in FIG. 2. The reaction rates of triplet state radical anion-cation pairs appear however to be strongly affected by weak magnetic fields (~0.01 T). This reaction is shown as reaction step 9 in FIG. 2. Furthermore it is known that the lifetime of triplet state radical anion-cation pairs can be increased by confining them in a membrane or in a micelle. In the present invention, the use of magnetic fields is employed to affect the rate of triplet-triplet annihilation reactions, and for modifying the spin state populations of charged and uncharged radical pairs.

SUMMARY OF THE INVENTION

It is an object of the present invention to provide a method and apparatus for elucidating reaction dynamics of photoreactive compounds from optical signals affected by an external magnetic field. In accordance with the invention, this object is achieved with a method and apparatus as described in the appended claims.

BRIEF DESCRIPTION OF THE DRAWINGS

The present invention will be better understood after reading a description of a preferred embodiment thereof made in reference to the following drawings in which.

DESCRIPTION OF A PREFERRED
EMBODIMENT OF THE INVENTION

In this invention, we propose to use a variable magnetic field to affect the reaction dynamics of photoreactive compounds in vivo. Since the Type I reaction pathway of an excited triplet state PS involves the production of radicals, their rates of formation and destruction can be perturbed by applying an external magnetic field (In the context of the present invention, the reader will appreciate that although the expression "magnetic field" is used, it also includes the expression "electromagnetic field", as the invention could also be used with LF and VLF fields with appropriate results). The rate of reaction of these species can be monitored by probing the tissue with a short-pulsed laser beam and detecting the back-reflected or transmitted light. If the wavelength of detection is same as the probing beam, the kinetics of absorbing transient species can be followed. If the wavelength of detection is different from the probing beam, the luminescence properties of excited state species can be tracked.

Correlations between tissue oxygen demand and the strength of the applied magnetic field can be determined in a controlled manner by measuring the luminescent emissions of singlet oxygen along with the fluorescent and phosphorescent emissions and absorption transients of the photosensitizer during photodynamic therapy. Furthermore, the occurrence of correlations between the perturbations in luminescent emissions of singlet oxygen and those of the photosensitizer allows for a means to assess tissue oxygen demand indirectly. The occurrence of such correlations thereby eliminates the need to directly measure weak singlet oxygen emissions and provides a practical means for clinical PDT monitoring.

By measuring the relative rates of radiative de-excitation over a broad time scale using a temporally resolved detection system (nanosecond to microsecond range), the ratio of singlet to triplet spin states of the transient species may be elucidated and followed. If this type of measurement is made over the course of a therapeutic session as a function of magnetic field strength and local tissue oxygen concentration (either with a pulse oximeter, an oxygen electrode, or by monitoring the luminescence emissions at 1269 nm (P-type delayed oxygen luminescence), precise information pertaining to the rate or extent of the Type II reaction pathway can be elucidated.

Figure 3:
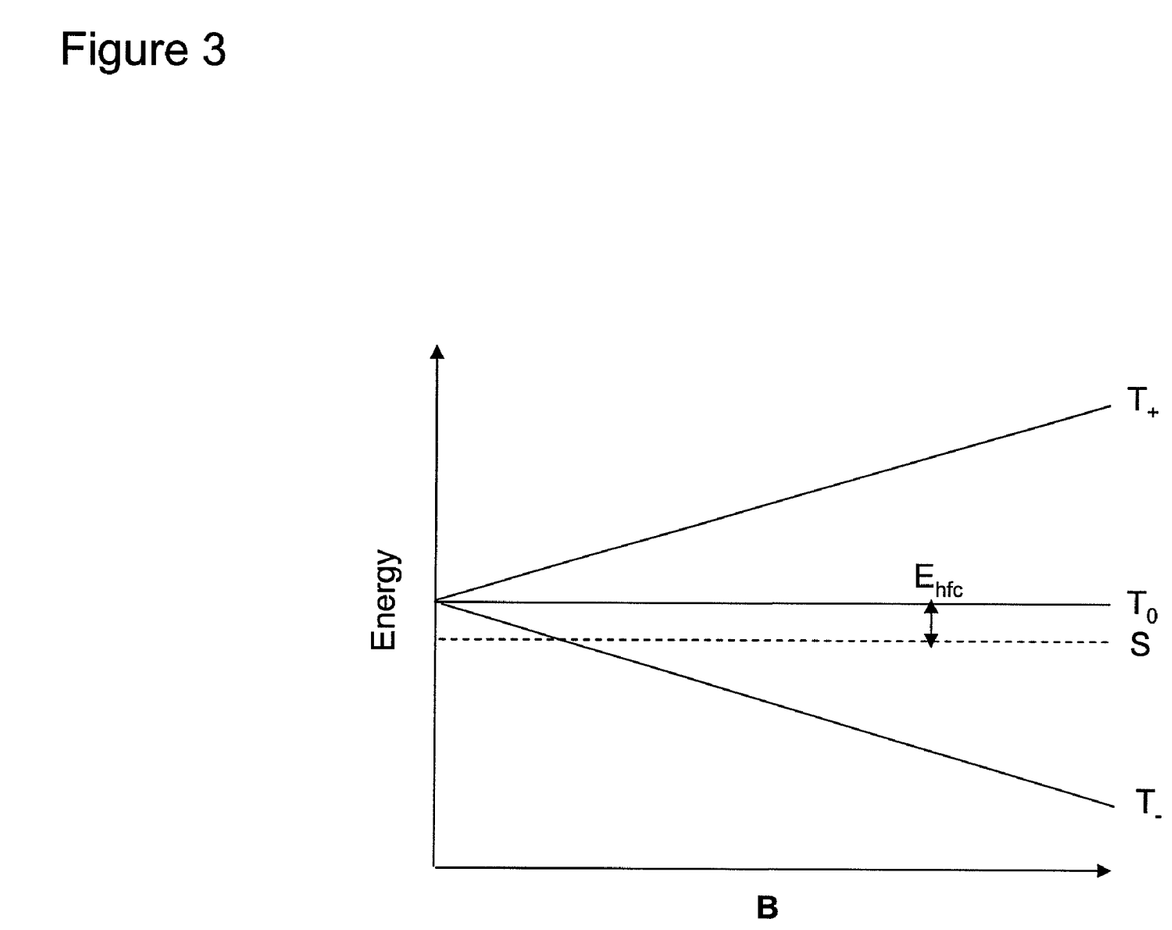
FIG. 3 is a visual representation of the Zeeman effect on a singlet state and a degenerate triplet state.

By measuring the nano- to microsecond scale luminescent decay rates of the transient species continuously over the course of a therapeutic session as a function of magnetic field strength, it is also possible to monitor changes in the local chemical environment of the tissue being irradiated. This can be done by measuring the ratio or differences in fluorescent lifetime, phosphorescent lifetime or their intensities registered at two different magnetic field strengths. Such qualities should vary depending on the local chemical environment of the tissue because the lifetime of the charged radical pairs depends on the local salvation sphere, pH and whether the ion pair is enclosed in a micelle (lysosome) or bound to a membrane. It is hypothesized that the rate of intersystem crossing between a triplet and singlet state cation anion radical pair, which have similar energies will be strongly affected by applying an external magnetic field (c.f. reaction step 9 in FIG. 2). When the magnetic field is applied, the electronic Zeeman splitting of the $T_\pm$ states removes the degeneracy of the three triplet magnetic sublevels as shown in FIG. 3. Since only the $T_0$ energy level remains unchanged in the presence of a magnetic field, the rate of triplet-singlet intersystem crossing due to the hyperfine coupling mechanism is reduced. As a consequence, the population ratio of singlet and triplet states of the excited PS changes. This in turn will affect the long time (μs) scale rates of radiative de-excitation manifested as delayed fluorescence. This general mechanism is known in the art as the radical pair mechanism.

Normally, the excited triplet state decays at a rate inversely proportional to its phosphorescence lifetime. However, when a magnetic field is applied, the rate of certain reactions, which involve species changing from a spin triplet state to a spin singlet state, will perturb the observed decay rate. Because singlet-to-singlet electronic transitions are quantum mechanically allowed, they are usually fast. Since fluorescence is the fast luminous decay process from singlet excited states to singlet ground states, these "fluorescent emissions" which seem to appear only after magnetic field is applied is referred to delayed fluorescence. In a CW measurement, the delayed fluorescence produced should increase the emission intensity.

Additionally, the local chemical environment may also be probed by tracking $B_{1/2}$ values over the course of the therapeutic session. The $B_{1/2}$ value is determined as the magnetic field strength at which the magnetic field effect reaches half its saturation value. As $B_{1/2}$ depends on the concentration of the radical and substrate species, it is expected that $B_{1/2}$ will change with the PS uptake and concentration. If the concentration of the PS in the tissue is estimated from the luminescence intensity, the bimolecular rate constant, $k_{ex}$ may be calculated for electron self-exchange reactions between a donor (D) or acceptor molecule (A) and the corresponding radical which is part of the spin-correlated geminate radical ion pair (reaction steps 10 and 11 of FIG. 2). The rate constant may be calculated using the following relation, $B_{1/2}([PS^*])=B_{1/2}(0)+k_{ex}[PS^*]h/2\pi\mu_B g$, where [PS*] is the concentration of the excited state photosensitizer, h is Planck's constant, $\mu_B$ is the Bohr magneton and g is the Landé splitting factor of the electron. It is hypothesized that $k_{ex}$ will vary with the chemical environment.

Figure 4:
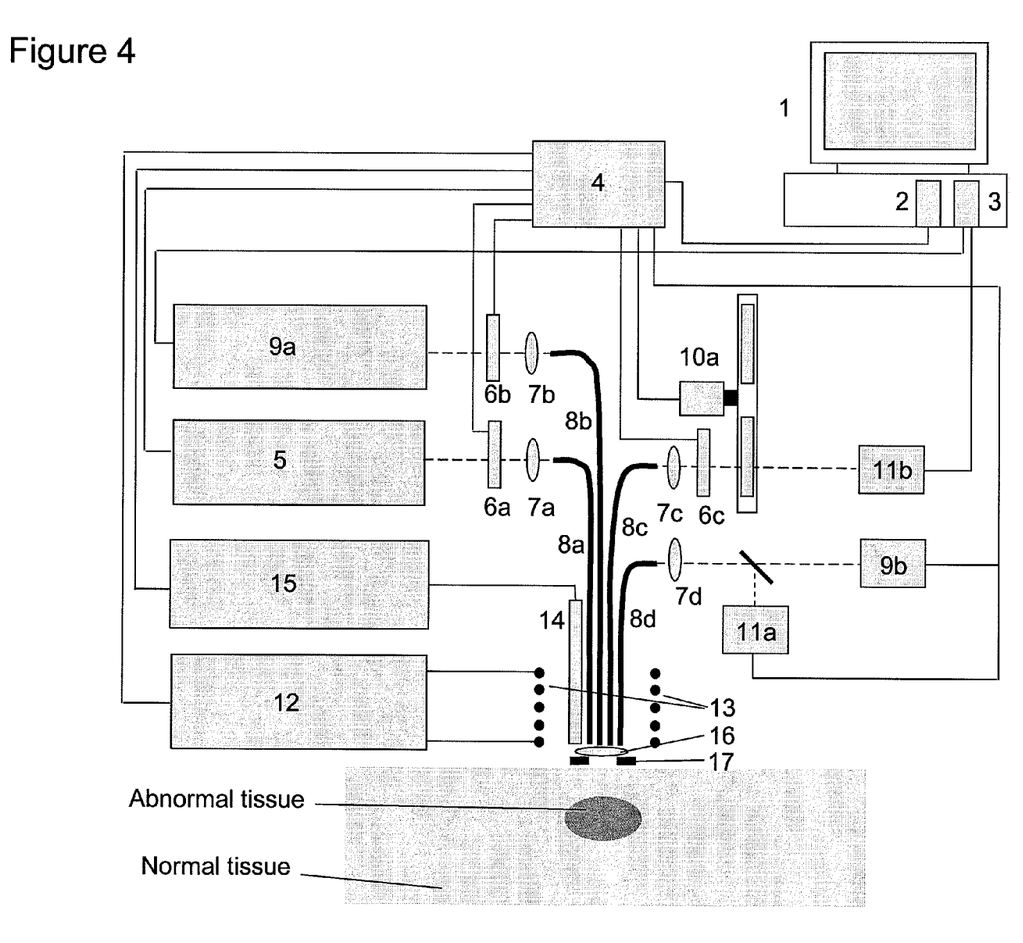
FIG. 4 is a schematic representation of an apparatus for determining in vivo organic reaction dynamics according to a preferred embodiment of the invention.

The basic apparatus, according to a preferred embodiment of the invention, used to follow the progress and kinetics of PDT active compounds is shown in FIG. 4 and includes the use of an adjustable field strength electromagnet situated near the tissue region which is being illuminated, an adjustable aperture CW therapeutic light source, a picosecond pulsed laser (probe beam), light collection optics and a time-resolved detection system. Furthermore, other monitoring probes such as a pulse oximeter, and/or an oxygen electrode may be incorporated into the device. For internal therapeutic applications, the illumination and collection optics may be in the form of a fiber-optic based endoscope which employs a micro-electromagnet near the distal end (see more particularly FIG. 7).

Referring now to FIG. 4, there is shown an apparatus according to a preferred embodiment of the present invention. The apparatus includes a probe head which contains a fiber optic cable 8, or bundle. Focussing or beam expansion optics 16 are provided for adapting the light beams to the particular needs. An iris 17 may be provided in front of the optics 16. The probe further includes a Hall effect probe 14 connected to magnetic flux meter 15. A Helmholtz coil 13 preferably surrounds the probe, the current for which is supplied by source 12.

In the embodiment of FIG. 4, four optical fibers are shown, although more or less may be required for any particular use.

Fiber 8a is connected to couplings optics 7a and in turn to an electric shutter and/or variable attenuator 6a. A light source 5 is directed towards attenuator 6a, and in the preferred embodiment, has wavelength L1 for inducing photodynamic therapy.

Fiber 8b is connected to coupling optics 7b and in turn to electric shutter and/or variable attenuator 6b. A nanosecond or modulated light source at wavelength L2 is directed into fiber 8b.

Fiber 8c is connected to coupling optics 7c and in turn to an electric shutter and/or variable attenuator 6c. A filter wheel, 10a, is placed between attenuator 6c and fast photomultiplier tube 11b. This fiber is the "detection" fiber.

The filter wheel is preferably provided with four filters which selectively let pass L1, F1 (the fluorescence wavelength band), P1 (the phosphorescence wavelength band), SOL (the singlet oxygen luminescence band centered at 1269 nm, and P2 which allows one to monitor the emissions on either side of the SOL band, depending on the use of the apparatus.

Fiber 8d is connected to coupling optics 7d and through a splitter to a detector 11a and a dual wavelength source 9b. This system comprises an optical pulse-oximeter which functions at wavelengths L3 and L4.

A controller hub 4 is preferably provided for interfacing the various components with computer 1, equipped with controller board 2 and single photon counting board or multiscalar board or frequency domain lock-in board 3. It should be understood that the specific components are not essential to the invention and can be replaced by other suitable components.

Figure 5:
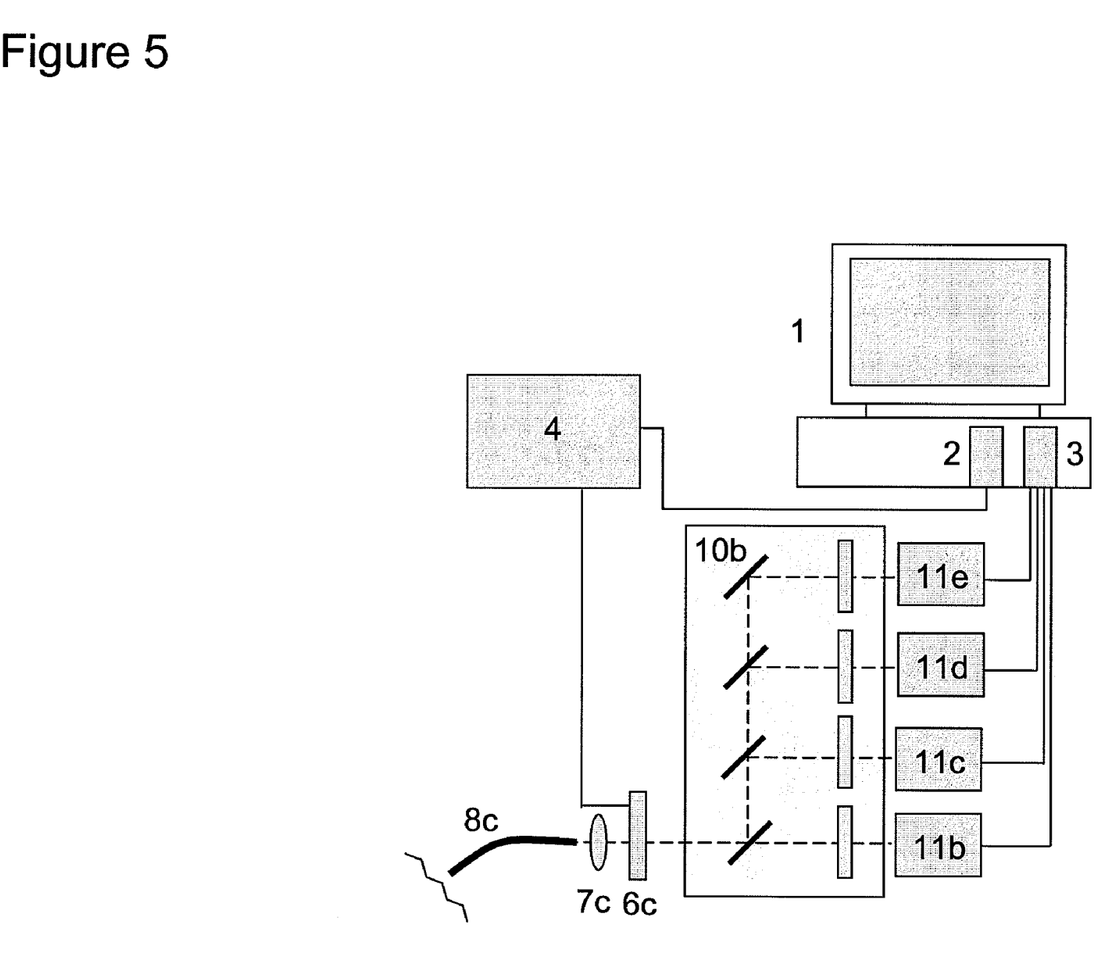
FIG. 5 is a schematic representation of a detection system which permits simultaneous optical measurements for use with a preferred embodiment of the apparatus of the invention.

Alternatively, multiple detectors can be used instead of a simple filter wheel to allow simultaneous detection as shown in FIG. 5. In this case, light from the detection fiber is selectively filtered and redirected toward each of the detectors (11b through 11e) by an optical system 10b. This optical redirection system can employ either a series of beamsplitters, cold and/or hot mirrors, a 1×4 fiber coupler or a quadra-furcated fiber-optic bundle. When multiple detectors are used, computer board 3 is able to handle inputs from multiple detectors either directly or with the aid of a router.

Figure 6:
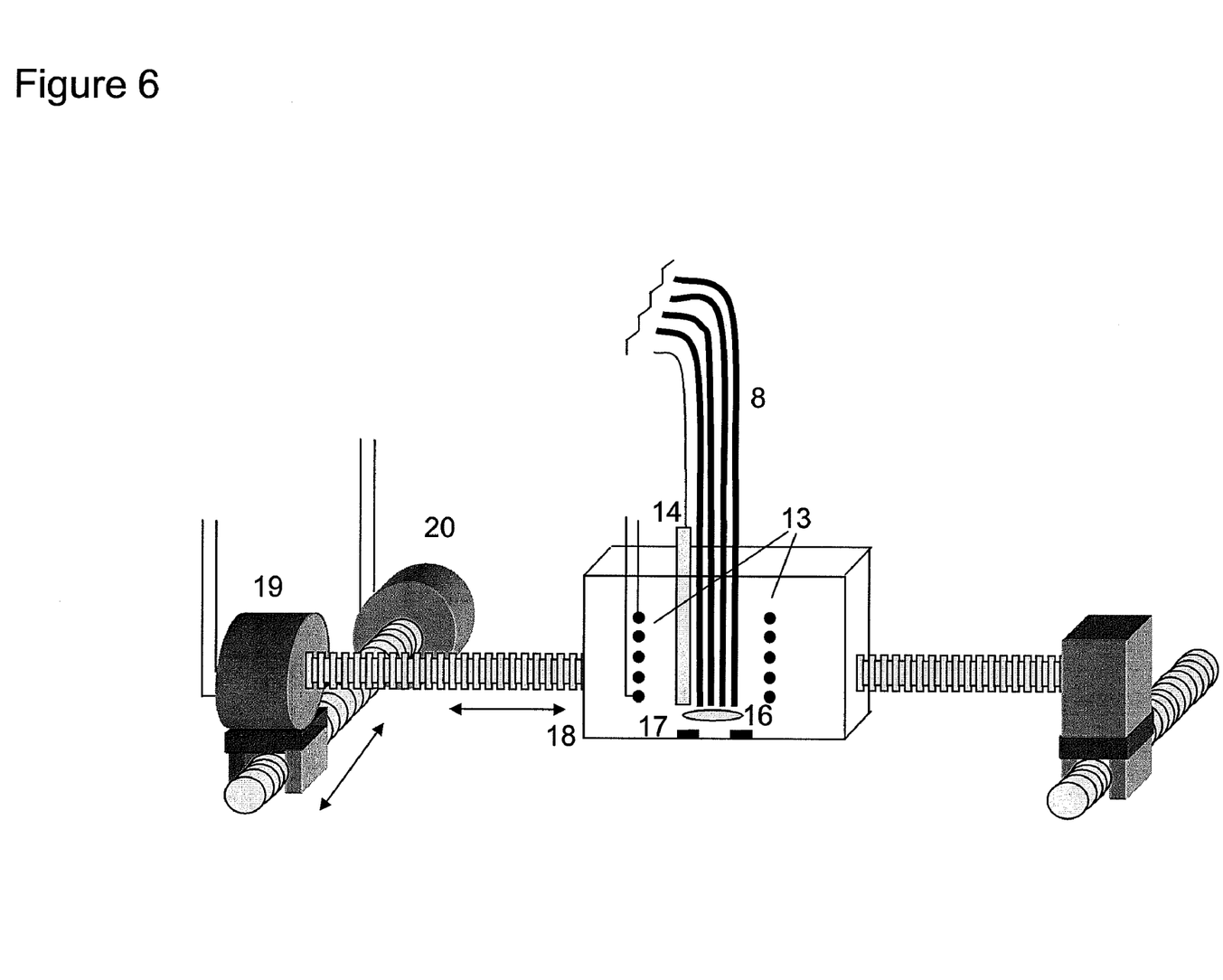
FIG. 6 is a schematic representation of an imaging embodiment of the probe for use with a preferred embodiment of the apparatus of the invention.

Furthermore, the apparatus may also be used in imaging applications, using a device shown in FIG. 6, which is mounted on a carriage 18, including stepper motors 19 and 20.

Figure 7:
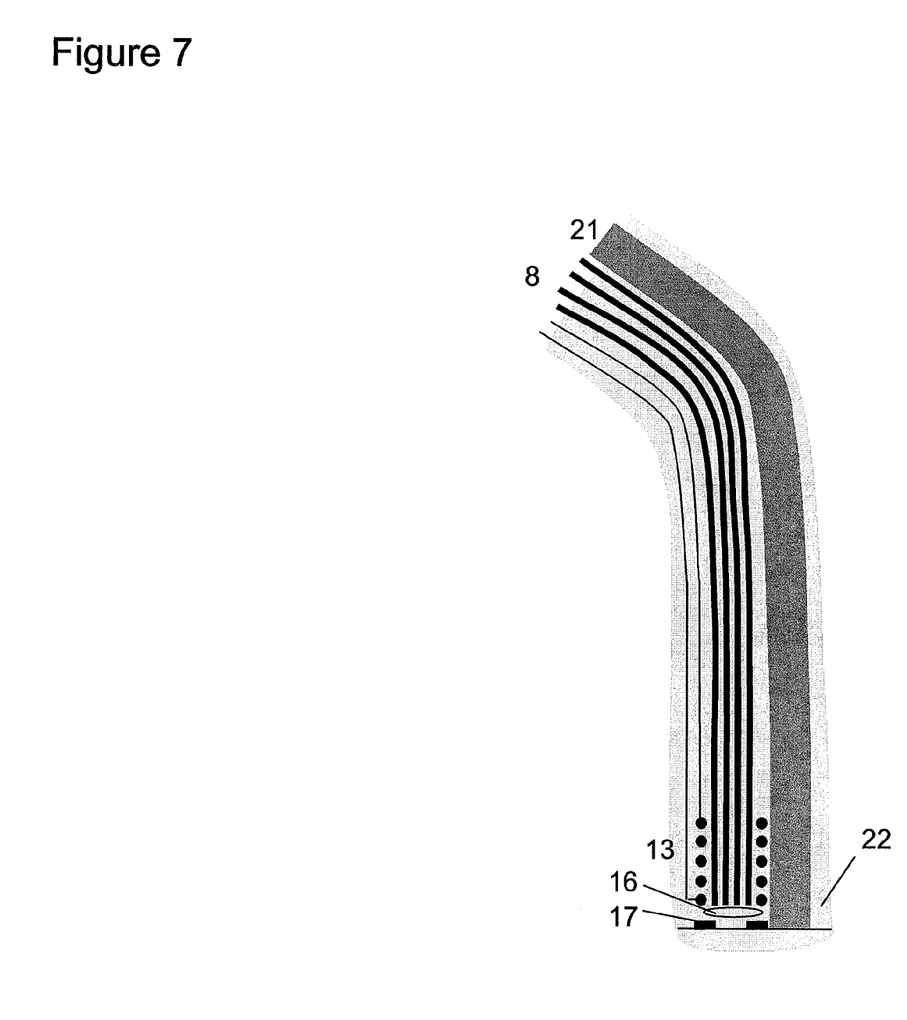
FIG. 7 is a schematic representation of an endoscopic embodiment of the probe for use with a preferred embodiment of the apparatus of the invention.

Although a "larger" version of the apparatus is shown in FIG. 4, the same principles can be applied to make a "smaller" version which can be used in endoscopic applications, as shown in FIG. 7. In this case, the distal end of the endoscope 23 is equipped with an imaging fiber optic bundle 22 and appropriate apparatus necessary for inducing, perturbing and monitoring photoreactive reactions.

Continuous wave techniques are covered by the teachings of the present invention. CW measurements may use either a pulsed or CW light source with a detector integrating light over a millisecond time scale. Alternatively, a time-correlated single photon counting (TCSPC) apparatus may be used and the pseudo-CW signal may be found by integrating under the time point spread function (TPSF). It should also be noted that the use of CW measurements might be of use for looking at delayed fluorescence in the region of interest.

For time resolved detection, a pulsed probe light source is appropriate and for frequency domain measurements, a modulated light source is to be used. For CW measurements, either a pulsed or CW light source may be used.

The types of light sources for the probe beam includes but are not limited to flashlamps, nanosecond or picosecond pulsed lasers with low repetition rates, pulsed LEDs, modulated LEDs, modulated light sources, and continuous wave sources.

Given the presence of a fiber bundle, one, two or a plurality of wavelength bands can be employed as the probe beam and/or therapeutic beam. It should be noted that the wavelengths for the probe beam and the therapeutic beams will be selected according to the specifics of the PDT and the reaction dynamics.

The two wavelengths used for the pulse oximeter (L3, L4) can be either fixed or adjustable (in case the PDT drug has a strong overlapping absorption band with oxy- and deoxy-haemoglobin. The wavelengths are typically 650 and 810 nm.

The apparatus can use a permanent magnet or one, two or a plurality of coils (for producing homogeneous fields about the ROI), the magnetic field may be turned on or off (square wave modulation), sinusoidally modulated, or its strength may be varied over the ROI by mechanical means (i.e. moving magnets). In the case of the coils, the coil diameter may be designed in such a way as to obtain a relatively uniform magnetic field around the ROI.

Additionally, a sinusoidally modulated magnetic field, which is generated electrically, may comprise a low frequency electromagnetic field (0-100 Hz).

Optical measurements can be made while the magnetic field is on, or off or while varying in strength.

Measurement Specifics

The reader will note that these operations may be done on a single point, two spatially different points (over a tumour region and over a normal tissue region) or over a plurality of points which allows line or 2D image maps to be constructed.

A description of the mode of operation for evaluating (and treating) a region of interest (ROI) according to a preferred embodiment follows. It should however be noted that the order is not necessarily crucial. What is important is to first calibrate the apparatus, second administer the drug (these could in some cases be done simultaneously), third irradiate the ROI and fourth perform the measurements.

1. Before administering the photoreactive agent into the system under study or treatment, irradiate the ROI with probe beam 2. Record the tissue fluorescence, phosphorescence, and absorption characteristics of the ROI at one or several wavelengths i.e. at L1, F1, P1, SOL, P2 providing baseline values $I_{0,L1}(t)$, $I_{0,F1}(t)$, $I_{0,P1}(t)$, $I_{0,P2}(t)$ where t refers to a nanosecond to microsecond time-scale
3. Turn off the probe beam
4. Record the tissue oxygenation and blood perfusion of the ROI (if applicable)
5. Administer the photoreactive agent
6. Irradiate the ROI with probe beam
7. Record the luminescence intensity and lifetime and absorption characteristics of the ROI at one or several wavelengths when B=0 Tesla i.e. at L1, F1, P1, SOL, P2 providing zero field values $I_{B=0,L1}(t)$, $I_{B=0,F1}(t)$, $I_{B=0,P1}(t)$, $I_{B=0,SOL}(t)$, $I_{B=0,P2}(t)$
8. Record the luminescence intensity and lifetime and absorption characteristics of the ROI at one or several wavelengths when B>0 Tesla i.e. at L1, F1, P1, SOL, P2 providing perturbed values $I_{B,L1}(t)$, $I_{B,F1}(t)$, $I_{B,P1}(t)$, $I_{B,SOL}(t)$, $I_{B,P2}(t)$
9. Repeat step 8 if more than one magnetic field strength is to be used
10. Turn off the probe beam
11. Record the tissue oxygenation and blood perfusion of the ROI (if necessary)
12. Process the data with the appropriate data processing methods
13. Determine if it is appropriate to turn on the therapeutic beam. This may be determined either manually or automatically. If done automatically, this decision is to be based on either tissue oxygenation and/or pharmacokinetic information.
14. Update and display the results on the processing unit
15. If the therapeutic beam is to be employed, it should turn on for a set time then turn off, then steps 6 through 13 should be repeated.

In the second preferred mode of operation, the method is the same as the first mode except that the probe beam and therapeutic beam use the same source and wavelength.

In a third preferred mode of operation, the probe beam and therapeutic beam use the same source and wavelength but the probe beam is substantially less intense than the therapeutic beam.

Data Processing Methods

As mentioned in the Measurement Specifics, the luminescence intensity and lifetime and absorption characteristics of the ROI are recorded at one or several wavelengths as a function of applied magnetic field strength over time (hereby referred to as the raw data).

The determination of fluorescent and phosphorescent lifetimes, and their background corrected intensity amplitudes are based on well-known techniques in the art. The exact technique will of course vary depending on whether time or frequency domain data is collected.

For the purposes of elucidating the reaction dynamics of photoreactive compounds, the raw data is further processed generating a set of processed data variables appropriate for displaying on the processing unit. The raw data is preferably transformed into the following set of processed data variables:
absorbance, $-\log(I_{L1}/I_{0,L1})$;
tissue oxygenation;
blood volume;
fluorescence intensity from PS, $I_{F1}-I_{0,F1}$;
phosphorescence intensity from PS, $I_{P1}-I_{0,P1}$;
fluorescence lifetime of PS, $\tau_{F1}$;
phosphorescence lifetime of PS, $\rho_{P1}$;
singlet oxygen emission intensity, $I_{SOL}-I_{P2}$;
luminescence lifetime of singlet oxygen, $\rho_{SOL}$;
triplet state lifetime of the PS ($\tau_T$) and singlet oxygen lifetime ($\tau_{SO}$), determined by fitting $I_{SOL}(t)$ to the equation:

$$I_{SOL}(t) = \frac{\tau_{SO}}{\tau_T - \tau_{SO}}\left[\exp\left(\frac{-t}{\tau_T}\right) - \exp\left(\frac{-t}{\tau_{SO}}\right)\right]$$

phosphorescence/fluorescence ratio, $I_{P1}/I_{F1}$ or $(I_{P1}-I_{0,P1})/(I_{F1}-I_{0,F1})$;
delayed fluorescence/phosphorescence ratio, $I_{B,P1}/I_{B=0,P1}$ or $(I_{B,P1}-I_{0,P1})/(I_{B=0,P1}-I_{0,P1})$;
fluorescence lifetime difference, $\Delta\tau_{F1}=\tau_{B,F1}-\tau_{B=0,F1}$;
phosphorescence lifetime difference, $\Delta\tau_{P1}=\tau_{B,P1}-\tau_{B=0,P1}$;
the value of the magnetic field strength at which the magnetic field effect reaches half it saturation value, $B_{1/2}$;
the bimolecular rate constant of electron exchange reaction, $k_{ex}$. This rate may be determined by the formula: $B_{1/2}([PS^*])=B_{1/2}(0)+k_{ex}[PS^*]$ h/$2\pi\mu_B$ g where, [PS*] is the photosensitizer concentration estimated from the luminescence intensity, h is Planck's constant, $\mu_B$ is the Bohr magneton, g is the Landé splitting factor of the electron, $B_{1/2}(0)$ is the extrapolated $B_{1/2}$ value at a zero concentration of PS obtained from a graph of $B_{1/2}$ versus [PS*] or assumed to be zero;
the correlation between tissue oxygenation and the singlet oxygen intensity;
the correlation between blood volume and the singlet oxygen intensity;
the correlation between the fluorescence lifetime difference and the singlet oxygen intensity;
the correlation between the phosphorescence lifetime difference and the singlet oxygen intensity;
the correlation between the phosphorescence/fluorescence ratio and the singlet oxygen intensity;
the correlation between the phosphorescence/fluorescence ratio and the singlet oxygen intensity;
the correlation between the delayed fluorescence/phosphorescence ratio and the singlet oxygen intensity;
the correlation between $k_{ex}$ and the singlet oxygen intensity.

The reader will appreciate that these correlations may be either performed in real-time or delayed by some time lag.

In order to elucidate the reaction dynamics of photoreactive compounds it is necessary to find trends in the spectroscopic data recorded over the ROI with the use of maps. The following data maps are the preferred means for conveying pertinent information to the user of the apparatus which permits reaction assessment over time:

static, two-dimensional spatial maps of the said processed data;
time-lapsed two-dimensional spatial maps of the said processed data;
one-dimensional time series maps of the said processed data;
one- or two-dimensional maps of the said processed data as a function of integrated light dose;
one- or two-dimensional maps of the said processed data as a function of drug dose;
one- or two-dimensional maps of the said processed data as a function of singlet oxygen production.

The use a variable magnetic fields to induce changes in time-resolved luminescence characteristics of a PS compound during a photodynamic therapy may have great utility in clinical settings. This approach may allow not only pharmaceutical companies to better understand the pharmacokinetic behaviour of drugs in development but allow for real time assessment of therapeutic treatment.

Although the present invention has been explained hereinabove by way of a preferred embodiment thereof, it should be pointed out that any modifications to this preferred embodiment within the scope of the appended claims is not deemed to alter or change the nature and scope of the present invention.

The invention claimed is:

1. An apparatus for elucidating reaction dynamics of photoreactive compounds present in a region of interest (ROI) of a tissue submitted to a substantially homogeneous magnetic field, said apparatus comprising:
    means for applying said substantially homogeneous magnetic field to said ROI, said means being external to said ROI and not in contact with said ROI;
    means for controllably varying the strength of said magnetic field according to a predetermined temporal pattern;
    a Hall-effect probe connected to a magnetic flux meter to measure the strength of said magnetic field;
    means for illuminating said ROI with a therapeutic optical beam, the combination of applying a magnetic field and illuminating said ROI with said therapeutic optical beam activating chemical reactions in said photoreactive compounds and affecting the subsequent evolution of said chemical reactions;
    means for illuminating said ROI with a probe optical beam;
    means for collecting light emitted from said ROI, to produce a collected light, said emitted light consisting of the portion of said probe optical beam that is transmitted through said ROI or the portion of said probe optical beam that is backscattered from said ROI according to a photoluminescence process;
    means for detecting said collected light over at least one predetermined wavelength band; and
    means for analyzing said detected light.

2. The apparatus according to claim 1, further including a pulse oximeter, an oxygen electrode, or both.

3. The apparatus according to claim 1, wherein said means for applying a magnetic field include at least one permanent magnet.

4. The apparatus according to claim 3, wherein said means for controllably varying the strength and temporal pattern of said magnetic field include means for moving said at least one permanent magnet.

5. The apparatus according to claim 4, wherein said temporal pattern of said magnetic field is selected from the group consisting of a square-wave modulation, a sinusoidal modulation, a constant value, a predetermined non periodic function of limited duration, or of any combination thereof.

6. The apparatus according to claim 1, wherein said means for analyzing said detected light are adapted to generate processed data, including luminescence lifetime calculations, difference and ratiometric processing, and correlating between at least two variables.

7. The apparatus according to claim 6, wherein said processed data is outputted visually as a map or a graph.

8. The apparatus according to claim 1, wherein said means for applying a magnetic field include at least one electrical coil.

9. The apparatus according to claim 8, wherein said means for controllably varying the strength and temporal pattern of said magnetic field include an electrical current source connected to said at least one electrical coil.

10. The apparatus according to claim 9, wherein said temporal pattern of said magnetic field is selected from the group consisting of a square-wave modulation, a sinusoidal modulation, a constant value, a predetermined non periodic function of limited duration, or of any combination thereof.

* * * * *